United States Patent [19]

Blumberg et al.

[11] Patent Number: 5,143,839
[45] Date of Patent: Sep. 1, 1992

[54] ASSAY OF ENDOPEPTIDASES AND NOVEL PURIFIED BACTERIAL ENZYME

[75] Inventors: Shmaryahu Blumberg, Rishon Le Zion; Anya Spungin, Givatayim; Fred E. Indig; Daniela B. Meir, both of Ramat Gan, all of Israel

[73] Assignee: Ramot Ltd., Tel-Aviv, Israel

[21] Appl. No.: 563,347

[22] Filed: Aug. 7, 1990

[30] Foreign Application Priority Data

Aug. 7, 1989 [IL] Israel .......................................... 91235

[51] Int. Cl.$^5$ .......................... C12Q 1/37; C12N 9/52
[52] U.S. Cl. ....................................... 435/220; 435/23; 435/24; 530/412; 530/416
[58] Field of Search ................... 435/180, 23, 24, 220; 530/412, 416

[56] References Cited

U.S. PATENT DOCUMENTS 4,146,432  3/1979  Hirohara .............................. 435/180

OTHER PUBLICATIONS

Vosbeck et al. (1973) The Proteolytic Enzymes of the K-1 ---J. Biol. Chem. 248: 6029–6034.
Vitale et al. (1986) Streptomyces–rimosus extracellular Proteases III, Isolation and Characterization of Leucine Aminopeptidase, Appl-Microbiol. Biotechnical: 23(6): 449–455.
Vosbeck et al., The Proteolytic Enzymes of the K-1 Strain of *Streptomyces griseus* Obtained from a Commercial Preparation (Pronase), Specificity and Immobilization of Aminopeptidase, *J. Biol. Chem.*, vol. 250, No. 10 pp. 3981–3987, 19075.
Vosbeck et al., Proteolytic Enzymes of the K-1 Strain of *Streptomyces griseus* Obtained from a Commercial Preparation (Pronase), Effect of pH, Metal Ions and Amino Acids on Aminopeptidase Activity, *J. Biol. Chem.*, vol. 253, No. 1, pp. 257–260, 1978.

*Primary Examiner*—Christine Nucker
*Assistant Examiner*—David R. Preston
*Attorney, Agent, or Firm*—Oblon, Spivak, McClelland, Maier & Neustadt

[57] ABSTRACT

The invention relates to highly purified aminopeptidases derived from Streptomycetes which are heat stable. There is further provided assay for the detection and quantitative determination of Neutral Endopeptidase 24.11 and Neutral Proteinase 24.4. A specific aminopeptidase is one derived from *Streptomyces griseus*, which is a calcium activated metalloprotein.

12 Claims, 5 Drawing Sheets

ASSAY OF ENDOPEPTIDASES AND NOVEL PURIFIED BACTERIAL ENZYME

The present invention relates to novel purified microbial source enzymes and to a highly sensitive assay for the qualitative and quantitative determination of neutral endopeptidases and neutral proteinases.

Amongst preferred bacterial enzymes which were purified there are Streptomyces derived enzymes, and more specifically, by way of example, a purified aminopeptidase derived from *Streptomyces griseus* which is a calcium activated zinc metalloprotein.

The invention further relates to a highly efficient process for the purification of enzymes of microbial origin, and especially of enzymes of the type mentioned above.

The invention further relates to the production of substrates which can be cleaved by certain enzymes which are to be determined, such as by neutral endopeptidases or enkephalinase (EC 3.4.24.11) and neutral proteinases 24,4; resulting in two moieties, one of which is subsequently cleaved by the bacterial enzyme, releasing a suitable marker which indicates the presence of the enzyme to be determined and its concentration. One form of assay is a kinetic one. The substrate is a short polypeptide protected at its one terminal by a protective group such as a bivalent succinyl group, glutaryl or similar blocking group, which advantageously results in water-solubility of this substrate. The polypeptide (generally 3 to 5 amino acids long) contains at its other end a chromophoric or fluorogenic group, adjacent to which there is located an amino acid which can be cleaved from such chromophoric or fluorogenic group by the bacterial enzyme.

Preferably the substrate is subjected to the action of the enzyme to be determined in the presence of the bacterial enzyme, so that the enzyme which is to be determined cleaves the substrate at a predetermined location, the subsequent cleavage of one of the moieties by means of the bacterial enzyme releasing a chromophoric group.

An example of a suitable substrate is Suc-Ala-Ala-Leu-NH-Np, which is cleaved by the enzymes such as neutral endopeptidase or neutral proteinases between the alanine and the leucine, resulting in two moieties, one of which is -Leu-NH-Np. In such probes the leucine can be replaced by phenylalanine, alanine and other amino acids, the preferred one being the leucine. The alanine adjacent the leucine can be replaced by glycine or other amino acids. After the cleavage, the Leu-NH-Np is attacked by the microbial enzyme, such as an aminopeptidase derived from any suitable Streptomycetes, releasing the chromophoric -NH-Np, which results in the coloration of the solution. The process is a kinetic one, and suitable calibration curves can be prepared for known concentrations of the neutral proteinase or peptidase. It is clear that other marker groups can be used instead of the -NH-Np group, such as for example methoxy naphthylanilide, methyl cumarinamide etc. The assay permits the rapid and very sensitive determination of such neutral endopeptidases and neutral proteinases. The measurements are carried out at predetermined time intervals or in an integrative manner.

The terminal blocking group is preferably a bifunctional one, such as a succinyl or glytaryl group which enhances water-solubility.

The assay of the present invention has many uses. For example, in acute lymphoblast leukemia, one of the proteins which appears on the cell surface is neutral endopeptidase 24.11 and this can be determined by a color reaction. The present invention also relates to a novel process for the purification of bacterial source enzymes, such as enzymes of Streptomycetes, which comprises a heat treatment to eliminate other enzymes, followed by removal of excess of calcium by gel filtration ultrafiltration or the like and ion exchange. The invention is described by way of example only with reference to the enzyme derived from *Streptomyces griseus*, and it ought to be understood that this description is of a non-limiting nature. The enzyme derived from this strain is a monomeric zinc metalloenzyme showing an apparent molecular mass of 33 kDa by sodium diodecyl sulfate polyacrylamide gel electrophoresis, and 21 kDa by gel-filtration on Superose 12.

INTRODUCTION

Neutral endopeptidase or enkephalinase (EC 3.4.24.11), a membrane-bound zinc metalloenzyme first isolated from rabbit kidney, is an ectoenzyme present on the surface of many cell types and is widely distributed in mammalian tissues including brain tissue. It shares basic elements of specificity and mechanistic properties with the well characterized bacterial neutral proteinase thermolysin (EC 3.4.24.4). The enzyme is implicated in the metabolism and regulation of a variety of peptides, e.g. the enkephalins, substance P and atrial natriuretic factor. Recently, a near identity in amino acid sequence between human endopeptidase 24.11 and the common acute lymphoblastic leukemia antigen (CALLA, CD 10) has been established, raising the possibility that it may be involved in yet other functions, related to cell differentiation and proliferation.

Calcium ions bind to the enzyme, $pK_{Ca}4.5$, and activate it ~6-fold when the substrate is Leu-4-nitroanilide (0.4 mM in 50 mM Tris.HCl, pH 8.0, 25° C.) protein.

Binding of $Ca^{2+}$ also contributes to the thermal stability of the protein. Sensitive metalloendopeptidase assays are usually based on a two-stage enzymatic reaction in which the endopeptidase attack of a blocked peptide substrate is followed by the rapid action of an aminopeptidase, added externally, to generate a highly absorbing chromophore or a fluorophor. An aminopeptidase employed in such assays is aminopeptidase M 1, 3-5, which has a high molecular mass and is difficult to purify from accompanying endopeptidases.

The extracellular fluid of *Streptomyces griseus* cultures is a rich source of a low molecular weight and highly active aminopeptidase that can be readily purified due to its thermostability. The activity of the enzyme can be modulated by the binding of calcium ions, providing an excellent model for the study of proteolytic enzyme activation by calcium ions.

Assay Methods

Aminopeptidase activity was assayed spectrophotometrically with 0.4 mM Leu-NH-Np in 50 mM Tris.HCl, pH 8.0 at 25° C., by following the continuous increase in absorbance at 405 nm due to the release of 4-nitroaniline, $\epsilon_{405}=10,600$ $M^{-1}$ $cm^{-1}$. Aminopeptidase activity of pooled fractions was examined in the presence of 1 mM $CaCl_2$.

One unit of activity hydrolyzes 1.0 umole of Leu-NH-Np per minute at 25° C., pH 8.0 under the specified conditions.

Specific activity is defined as units/$A_{280}$, where $A_{280}$ is the absorbance of the enzyme solution at 280 nm, or as units/mg protein. In addition, the activity of the purified enzyme towards. Ala-NH-Np and Lys-NH-Np, both at 0.4 mM in 50 mM Tris.HCl, pH 8.0 was examined.

Gel-Filtration

Gel-filtration was carried out on a Superose 12 column (1.0×33 cm) mounted on an HPLC system (Waters). Elution was carried out in 50 mM Tris.HCl-200 mM NaCl, pH 7.8 at a rate of 0.3 ml/min and protein was detected by absorbance at 229 nm.

Zn content was determined on an AA-775 Atomic Absorption Spectrophotometer (Varian). Mn and Co were determined in a GTA-95 Graphite Tube Atomizer (Varian) coupled to the AA-775 spectrophotometer.

Purification of *Streptomyces griseus aminopeptidase*

*Streptomyces griseus* extracellular protease preparations (pronase) contain very strong aminopeptidase activity which is stable at 70° C., unlike the other proteolytic activities in the mixture. This selective thermostability of the aminopeptidase has been exploited for a rapid and convenient purification of the enzyme.

Figure 1:
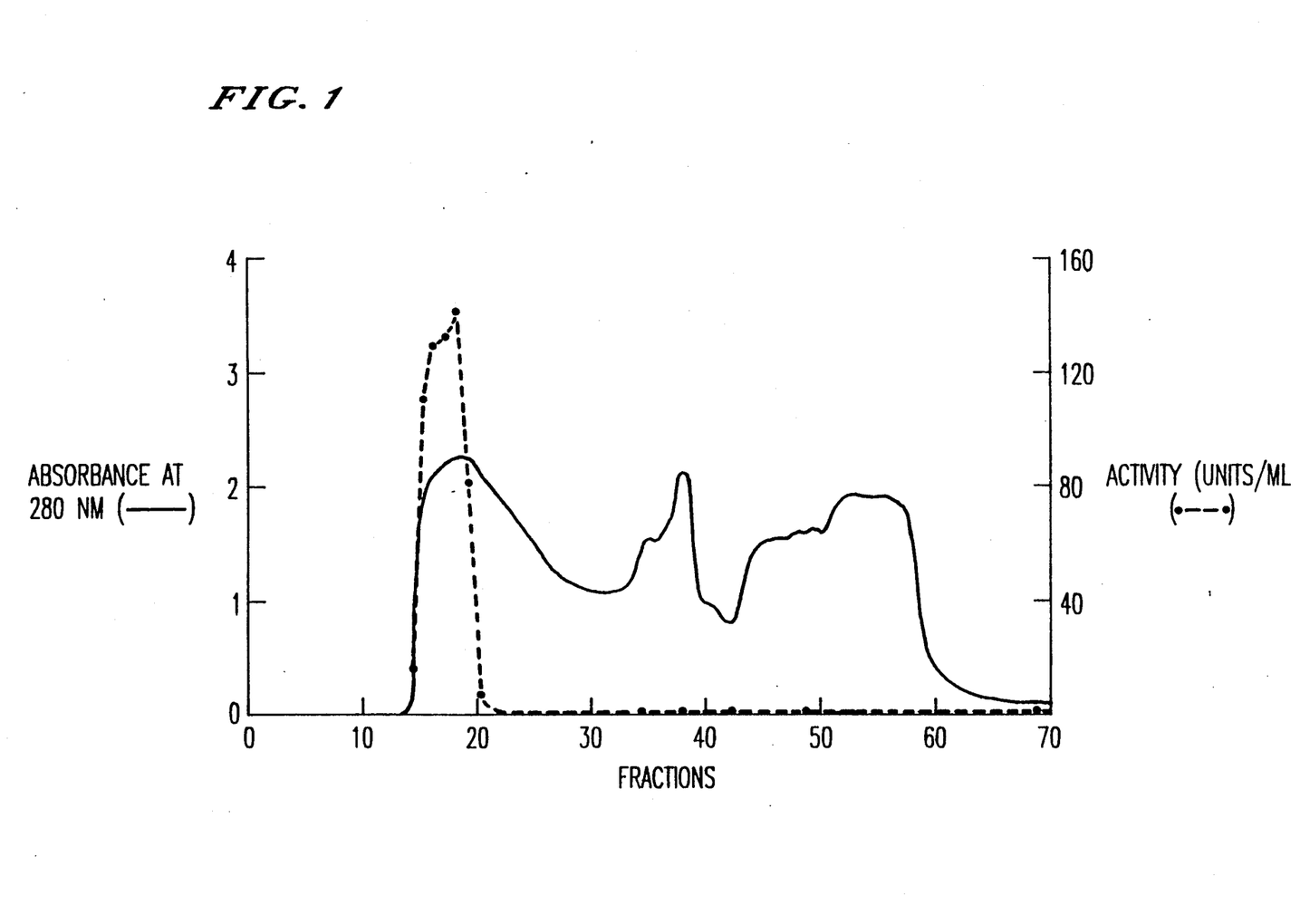

Heating of the *Streptomyces griseus* protease mixture at 69° C. for 5 h, results in a dramatic loss of all proteolytic activities except the aminopeptidase activity (Tables 1 and 2). Gel-filtration of the mixture on Bio-Gel P-4 column at low ionic strength elutes the aminopeptidase at the void volume and separates it from other proteases that underwent degradation and/or inactivation during heating as well as from excess calcium ions present in large amounts in the original preparation (FIG. 1).

Purification using different batches of starting material performed at room temperature, yields similarly active enzyme. A typical purification process is given below.

Heat Treatment 1 g and 300 mg of protease type XIV (Pronase E, containing 25% calcium acetate, Sigma), was dissolved in a 26 ml solution containing 50 mM Tris.Hcl-100 mM NaCl, pH 8.0, and the solution was incubated at 69° C. for 5h, then kept at 4° C. overnight and centrifuged at 3000 g for 10 min to remove slight precipitate.

Bio-Gel P-4 gel filtration

Most of the heated protease solution (21.7 ml) was gel-filtered on a Bio-Gel P-4 column (2.6×42.5 cm) equilibrated and eluted with 10 mM Tris.Hcl-20 mM NaCl, pH 8.0 at a rate of 1.3 ml/min and 5.2 ml fractions were collected. The early fractions, excluded from the gel, containing most of the aminopeptidase activity were pooled (26 ml) and kept at 4° C.

DEAE-Sepharose fast flow ion-exchange chromatography

The pooled fraction of the Bio-Gel P-4 column was brought to pH 9.0 by adding 1N NaOH and the solution (24.5 ml) was applied on a DEAE-Sepharose Fast Flow Column (1.6×33 cm), preequilibrated and eluted with 10 mM Tris.Hcl-20 mM NaCl, pH 9.0 After approximately 50 ml, when a 280 nm absorbing material emerged from the column, 5.0 ml fractions were collected at a rate of 1.25 ml/min. After approximately 300 ml, the eluting buffer was changed to 10 mM Tris.Hcl-60 mM NaCl, pH 9.0 and elution was continued until a large peak followed by a smaller and wider peak, both containing aminopeptidase activity, emerged from the column. The aminopeptidase emerging in the large early peak is designated *Streptomyces griseus* aminopeptidase I (*S. griseus* API) and that in the smaller retarded peak *S. griseus* aminopeptidase II (*S. griseus* APII). A change in the eluting buffer to 10 mM Tris.Hcl-90 mM NaCl, pH 9.0 resulted in the elution of only trace amount of additional aminopeptidase activity that was discarded.

The fractions of the first major peak (*S. griseus* API) were pooled by discarding the material absorbing up to about 20% of the maximal absorbance at 280 nm, at both the ascending and descending limbs of the peak and of the second minor peak (*S. griseus* APII) by discarding up to about 40% of the maximal absorbance at 280 nm, at both sides of the peak.

The pH of each pooled enzyme peak (30 ml for the first peak and 55 ml for the second peak) was lowered by adding 1M Tris.Hcl, pH 7.2 (10 μl/ml) to a final concentration of 20 mM Tris.Hcl-60 mM NaCl, pH 8.2.

For further characterization of the aminopeptidase the pooled peaks were dialyzed extensively (3-4 1 liter changes during 2-3 days) against distilled water (pH~5.5).

The purified aminopeptidase (*S. griseus* API) is heat stable retaining ~80% of the original activity after 5 h heating at 69° C. in the presence of $10^{-2}$M $CaCl_2$ (20 mM Tris.Hcl-60 mM NaCl-10 mM $CaCl_2$, pH 7.7) and ~60% of the original activity in the absence of added $Ca^{2+}$. Heating at 69° C. prior to use eliminate trace endopeptidases far below their limits of detection.

Purity of the aminopeptidase

Demonstrated by SDS PAGE.

Apparent Molecular Mass of the Aminopeptidase

The molecular mass of *S. griseus* API as deduced from SDS gels is 33 kDa. *S. griseus* APII is slightly more retarded on the gel, corresponding to an apparent molecular mass of 34 kDa.

Gel-filtration on Superose shows apparent molecular mass of 21 kDa an d22.5 kDa for *S. griseus* API and *S. griseus* APII, respectively.

Modulation of Streptomyces Aminopeptidase Activity by Calcium Ious

Figure 4:
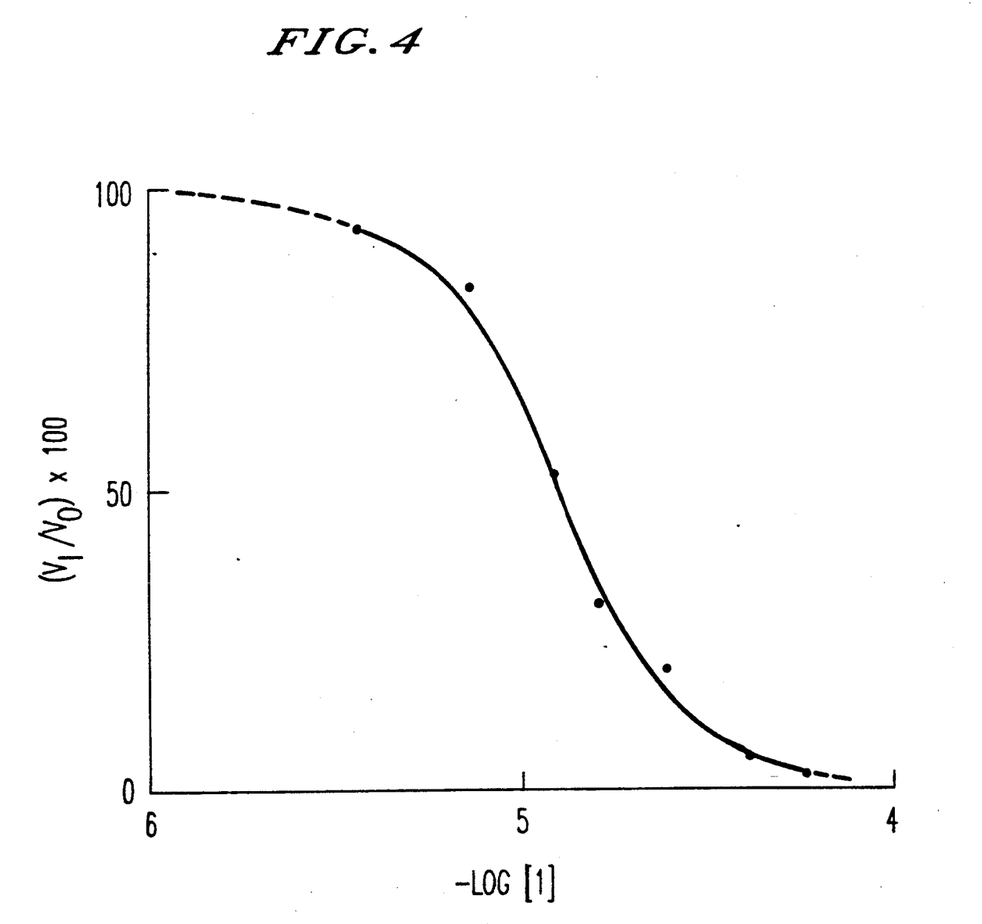

Addition of $Ca^{2+}$ to *S. griseus* API (and *S. griseus* APII) increases the Leu-NH-Np activity of the enzyme ~6-fold (FIG. 4). The $pK_{Ca}$ of the activation process is 4.5 (FIG. 4).

Transition Metal Content

Based on protein content estimated by amino acid analysis and on a molecular mass of 21 kDa deduced from gel-filtration on Superose 12, the zinc content of extensively dialyzed *S. griseue* API preparations is 1.05±0.14 g atom zinc per mole enzyme. Manganese and cobalt are absent in the samples (<0.01 g atom per mole enzyme. The metal analysis suggests that *S. griseus* API (and *S. griseus* APII) is a zinc metalloenzyme.

*Streptomycee griseus* proteases are usually purified in the presence of $Ca^{2+}$ ions because several of these enzymes require $Ca^{2+}$ for stability. By assuming that this requirement does not necessarily pertain to *S. griseus AP* and on the other hand that $Ca^{2+}$ binds to the enzyme (see below), we have removed excess $Ca^{2+}$ present in the starting preparation by gel-filtration (FIG. 1). Removal of excess $Ca^{2+}$ that binds to the enzyme reduces the net positive charge of the protein. This allows tight binding of the enzyme to an anion-exchange column and subsequent elution by increasing salt concentration (FIG. 2), thereby resulting in a remarkable purification of the enzyme (Tables I and II). Thus, heat treatment of the preparation and removal of excess $Ca^{2+}$ prior to the ion-exchange chromatographic step are the two key elements in the purification procedure here presented.

The purified S. griseus AP has an extremely high specific activity when assayed with the commonly used substrate Leu-NH-Np. It is highly purified from endopeptidases (Table 2) and, therefore, most suitable for two-stage assays of bacterial and mammalian metalloendopeptidases. When added to the substrate Suc-Ala-Ala-Leu-NH-Np it provides an excellent additive for assaying thermolysin and the membrane-solubilized bovine kidney metalloendopeptidase, often named enkephalinase.

Figure 2:
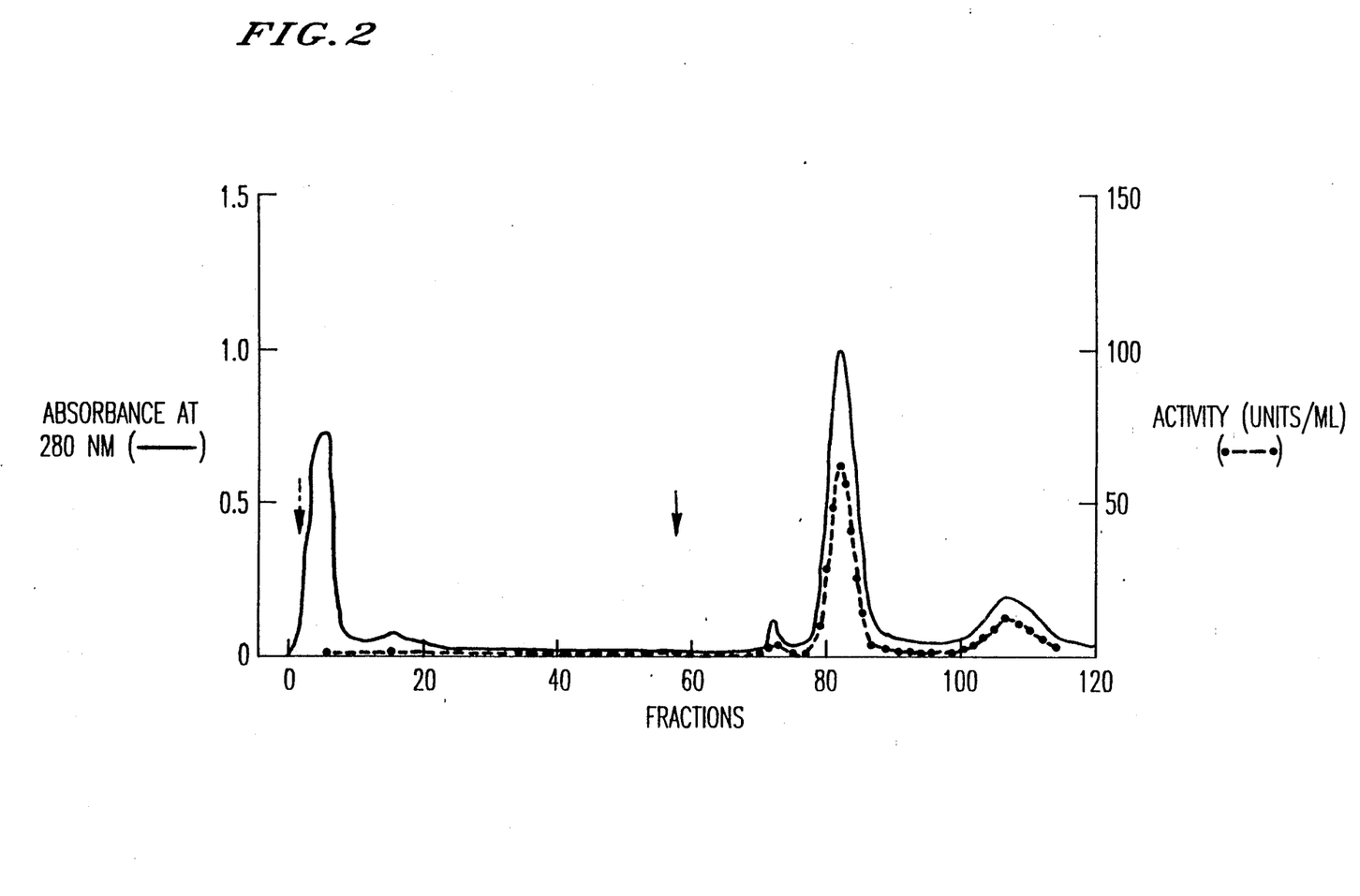

Streptomyces griseus aminopeptidase represents a rare example of an extracellular enzyme where $Ca^+$ binding modulates the activity of the enzyme and not only increases its stability.

material emerged from the column, 5.0 ml fractions were collected (dotted arrow). After approximately 300 ml the eluting buffer was changed to 10 mM Tris.Hcl-60 mM Nacl, pH 9.0 (arrow). Absorbance at 280 nm (—). Leu-NH-Np activity in the absence of added $Ca^{2+}$ ( ).

Figure 3:
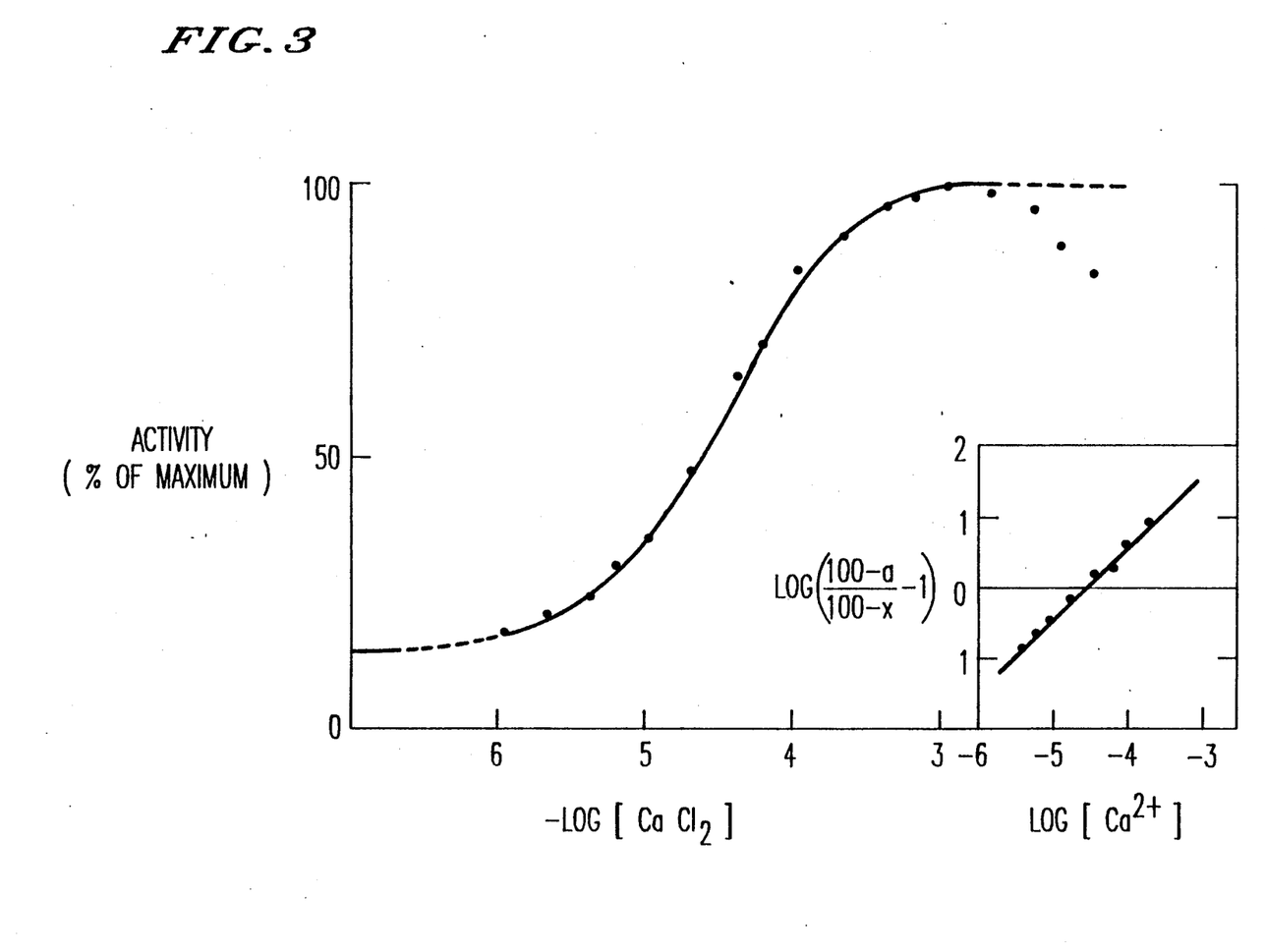

FIG. 3—Modulation of Streptomyces griseus aminopeptidase activity by $Ca^{2+}$. S. griseus API dialyzed extensively against distilled water, was diluted to a concentration of 1.3 uM enzyme in 20 mM Tris.HCl-60 mM NaCl, pH 8.0. Two $\mu$l aliquots were added to 2.5 ml of 0.4 mM Leu-NH-Np in 50 mM Tris.Hcl, pH 8.0, supplemented with varying concentrations of $CaCl_2$ prior to addition of the enzyme. Activity was measured at 25° C., by following the increase in absorbance at 405 nm due to the release of 4-nitroaniline. The maximal activity at $10^{-3}$ $Cacl_2$ is taken as 100%. The mark on the ordinate represents the activity in the absence of added $Ca^{2+}$. Activity upon addition of $Ca^{2+}$ at the specified concentrations ( ). Inset: Hill plot of the activation of S. griseus API by $Ca^{2+}$.

FIG. 4—Inhibition of Streptomyces griseus aminopeptidase by 1,10-phenanthroline. S. griseus API dialyzed extensively against distilled water was diluted to a con-

TABLE 1

Summary of Purification of Streptomyces griseus Aminopeptidase
The starting material is protease type XIV, Sigma, dissolved in 50 mM Tris.HCl-100 mM NaCl, p 8.0, 50 mg/ml. The volumes are corrected for outdrawn samples. The activities are assayed in presence of 1 mM $CaCl_2$.

| Purification step | Vol(corr) (ml) | Absorbance ($A_{280}$) | Activity Units/ml | Total | sp act Units/$A_{280}$ | Recovery of activity (%) |
|---|---|---|---|---|---|---|
| Starting material | 20.45 | 52.9 | 1365 | 27910 | 25.8 | 100 |
| 69° C. heating, 5 h | 20.45 | 45.3 | 856 | 17510 | 18.9 | 63 |
| BioGel P-4 gel-filtration | 24.5 | 4.8 | 602 | 14750 | 125 | 53 |
| DEAE-Sepharose Peak I | 30 | 0.87 | 266 | 7980 | 305 | 29 |
| Chromatography Peak II | 55 | 0.145 | 46 | 2530 | 317 | 9 |

TABLE 2

Residual Proteolytic Activities in Streptomyces griseus Aminopeptidase
Proteolytic activities are measured on the pooled solutions. The values in parentheses are limits of detection based on practical parameters of the continuous assays, i.e. enzyme aliquots of up to 100 ul, reaction time 1 h, and change in absorbance of 0.005 for NH—Np substrates and 0.002 for FA substrates.

| Purification step | PhCO—Arg—NH—Np | FA—Gly—Leu—$NH_2$ | Suc—Phe—NH—Np | FA—Gly—Leu |
|---|---|---|---|---|
| Starting material | 100 | 100 | 100 | 100 |
| 69° C. heating, 5 h | 0.004 | 0.002 | 0.4 | 2.5 |
| DEAE-Sepharose Peak I | N.D.[a](0.001) | N.D(0.0006) | N.D(0.1) | N.D(0.2) |
| Chromatography Peak II | N.D(0.001) | N.D(0.0006) | N.D(0.1) | N.D(0.2) |

[a]N.D., not detectable.

FIG. 1—Gel-filtration chromatography of heat-treated Streptomyces griseus protease mixture on a Bio-Gel P-4 column. Streptomyces griseus solution preheated at 69° C. for 5 h and centrifuged was passed on Bio-Gel P-4 column (2.6×42.5 cm), at a rate of 1.3 ml/min. The absorbance at 280 nm was monitored continuously and 5.2 ml fractions were collected. Absorbance at 280 nm (—), Leu-NH-Np activity in the absence of added $Ca^{2+}$ ( ).

FIG. 2—Anion-exchange chromatography of gel-filtered Streptomyces griseus protease mixture on DEAE-Sepharose Fast Flow column. The pooled aminopeptidase fraction from the Bio-Gel P-4 column was brought to pH 9.0 by NaOH and passed on the DEAE-Sepharose column (1.6×33 cm) at a rate of 1.25 ml/min. The absorbance was monitored continuously and after approximately 50 ml, when the first 280 nm absorbing centration of 1.3 uM enzyme in 20 mM Tris.HCl-60 mM NaCl, pH 8.0. Two $\mu$l aliquots were added to 2.5 ml of 0.4 mM Leu-NH-Np in 50 mM Tris.HCl, pH 8.0, the reaction followed for 5 min and the inhibitor was added. Activity in the absence of the inhibitor is taken as 100%. Relative activity upon addition of 1,10-phenanthroline at the specified concentration ( ).

Figure 5:
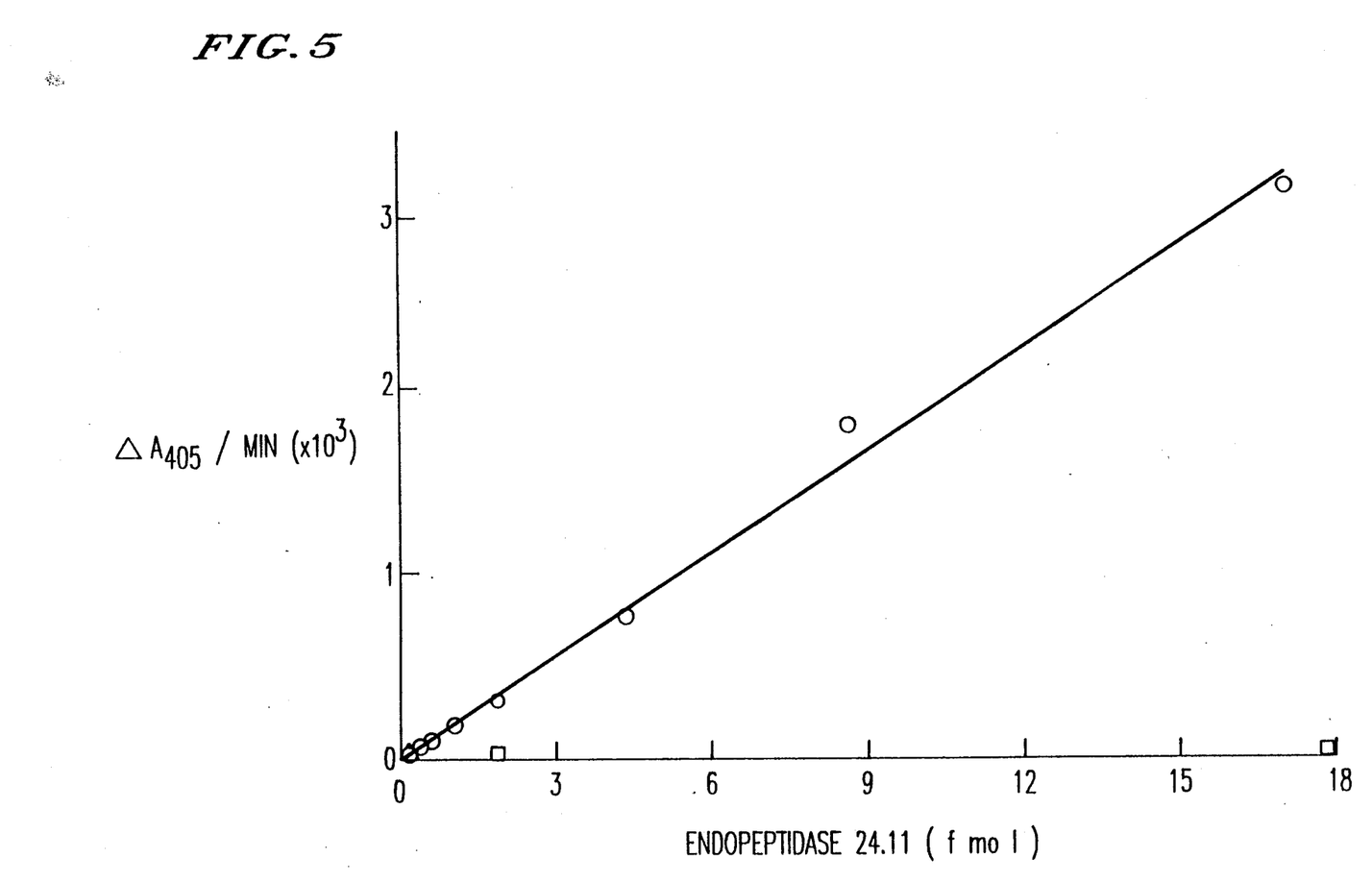

FIG. 5 is a graph plotting the enzymatic activity of endopeptidase 24.11 on 0.4 mM Suc-Ala-Ala-Neu-NH-Np at pH 7.5 against absorbance at 405 nm, where "O" represents the increase in the absorbance upon addition of enzyme, " " represents the inhibition of the reaction 1.8 $\mu$M phosphoramidon, and " " represents absorbance of the substrate and aminopeptidase alone.

THE ASSAY

Substrate

Suc-Ala-Ala-Leu-NH-Np was prepared by stepwise addition of two Ala residues to Leu-NH-Np (Sigma) via reaction with Boc-Ala-ONSu and deblocking of the Boc groups with trifluoroacetic acid, followed succinylation with Suc$_2$O. The product was recrystallized from 20% ethanol, overall yield 32%; mp 212°-214°; TLC (Silica-gel plates coated with fluorescent dye, Kieselgel 60F$_{254}$, 0.2 mm thick, Merck) gave a single spot: R$_F$=0.86 (n-butanol/acetic acid/pyridine/water=4:1:1:2); HPLC (C$_8$ column, 4.6×250 mm (5 μm), protected with a C$_8$ guard column, Supelco) showed >98% purity (4.1 mM phosphoric acid/triethylamine, pH 3.3 in acetonitrile, 60:40); analysis calculated for C$_{22}$H$_{31}$N$_5$O$_8$, C=53.54; H=6.33; N=14.19; found: C=53.48; H=6.25; N=13.87.

Enzymes

*Streptomyces griseus* aminopeptidase was purified to homogeneity from pronase E (Sigma) by heat treatment followed by gel-filtration and anion-exchange chromatography as set out above. Endopeptidase 24.11 from bovine kidney was purified by Triton X-100 extraction, followed by DEAE-Sepharcse Fast Flow, concanavalin A-Sepharose, Q-Sepharose and hydroxylapatite chromatographic procedures.

*Bacillus cereus* (X-3 DSM 3101, German Collection of Microorganisms, Braunschweig, FRG) containing the neural proteinase were obtained by overnight cultivation in a rich medium supplemented with calcium chloride.

Neutral endopeptidase and neutral proteinase activities were assayed by the two-stage assay using the synthetic substrate Suc-Ala-Ala-Leu-NH-Np supplemented with *Streptomyces griseus* aminopeptidase, usually 6-7 μg/ml. Assays were performed in 0.1M NaCl-0.05M Tris.HCl, pH 7.5 at 25° C., unless otherwise stated, with or without 0.01M CaCl$_2$. Assay volume was 1 ml or 2.5 ml when using a Varian Techtron spectrophotometer or 0.2 ml at 23° C. when performed with microplates (Munc Immuno Plate II F) using a Kinetic Microplate Reader (Molecular Devices Corp.). Activity was measured by following the increase in absorbance at 405 nm, due to the release of 4-nitroaniline, E$_{405}$=10,600M$^{-1}$cm$^{-1}$ [14]. Molar concentration of thermolysin was estimated using A$_{280}$ 1% =17.65 [15] and molecular mass of 34,600 Da [16]; molar concentration of bovine kidney neutral endopeptidase by protein determination and molecular mass of 90 kDa, deduced from SDS PAGE. Both endopeptidase 24.11 from bovine kidney and thermolysin cleave the Ala-Leu bond of the compound at a very fast rate (Table 3). The Leu residue of the substrate interacts with the major hydrophobic specificity sites of the enzymes (S'$_1$), whereas the two Ala residues interact with additional subsites (S$_1$, S$_2$), thereby contributing to catalysis and/or binding. Even the 4-nitroaniline leaving group probably interacts with the enzyme at subsite S'$_2$. Previously reported assays of endopeptidase 24.11 usually utilized a hydrophobic Phe residue, but Leu seems preferable in reaching higher k$_{cat}$ values. The rapid hydrolysis of the Leu residue is also preferable for the present two-stage assay utilizing Steptomyces aminopeptidase, since this enzyme very rapidly hydrolyzes the product of the endopeptidase attack, Leu-NH-Np. The rapid hydrolysis coupled with K$_m$ values in the 1 mM range and overall k$_{cat}$/K$_m$ values in the 10$^6$M$^{-1}$s$^{-1}$ range (Table 3), render the substrate most suitable for detailed kinetic investigations of the enzymes and for detection of the 24.11 and 24.4 classes of enzymes in mammalian tissues and in bacterial extracellular fluids, respectively.

Using microplates for enzyme detection, purified bovine kidney endopeptidase 24.11 was readily assayed at below 1×10$^{-15}$ moles enzyme and the assay is linear over a wide range of enzyme concentrations (FIG. 5). This sensitivity exceeds immunoassay levels of detection and may substitute and/or supplement it in studies of CALLA which is nearly identical with human endopeptidase 24.11.

Human neutrophils from a healthy donor (5×10$^5$ cells/ml) hydrolyze the substrate (0.4 mM, pH 7.5) at a fast rate ~1.3 nmoles/min/10$^6$ cells. Assuming that the bovine kidney and human neutrophil enzymes have similar activities, the above rate would amount to ~1.5×10$^5$ active endopeptidase 24.11 enzyme molecules per cell. However, detailed comparisons of the activities of purified endopeptidase 24.11 from different species and from different tissues, using a variety of substrates, are still required.

Using the above microplates for enzyme detection, 5×10$^3$ neutrophils were readily measured for their endopeptidase 24.11 activity.

Like other previously reported substrates for endopeptidase 24.11, the substrate employed may, in principle, be hydrolyzed by chymotrypsin-like enzymes. To assess the contribution of the neutral endopeptidases and neutral proteinases 1 the observed color development, the specific inhibitor of these classes of enzymes phosphoramidon was added (Table 4). The inhibitor completely abolishes the activity of the purified enzymes, and strongly inhibits the enzymatic reaction displayed by the intact neutrophils or by the bacterial culture used (Table 2).

Human neutrophils and leukemic lymphoblasts are high expressors of endopeptidase 24.11, the former cells probably requiring the enzyme to act upon chemotactic peptides. The sensitivity of the method presented here, however, allows detection of the enzyme on other cell types, expressing the enzyme at a much lower level, and may therefore help to investigate its roles under normal cell function.

TABLE 3

Kinetic parameters for bovine kidney neutral endopeptidase 24.11 and for thermolysin hydrolysis of Suc~Ala~Ala~Leu~NH~Np.

| Enzyme | (S) Range (mM) | k$_{cat}$ (s$^{-1}$) | K$_m$ (mM) | k$_{cat}$/K$_m$ (M$^{-1}$s$^{-1}$ × 10$^{-6}$) |
|---|---|---|---|---|
| Endopeptidase 24.11 | 0.04-4.0 | 1.2 × 10$^2$ | 0.15 | 0.80 |
| Thermolysin | 0.4-4.0 | 1.2 × 10$^3$ | 4.2 | 0.29 |

Reactions were carried out in the presence of 10 mM CaCl$_2$ at pH 7.5, 25° C. 2.2×10$^{-9}$M and 3.0×10$^{-10}$M of endopeptidase 24.11 and therymolysin, respectively, were used. Values of k$_{cat}$ and K$_m$ were determined by Lineweaver-Burk plots.

TABLE 4

Inhibition of neutral endopeptidases 24.11 and neutral proteinases 24.4 activities by phosphoramidon.

| Enzyme | Phosphoramidon (μM) | % Inhibition |
|---|---|---|
| Endopeptidase 24.11 | 3.6 | >99 |
| Thermolysin | 18.0 | >99 |
| Human neutrophils | 3.6 | >95 |

TABLE 4-continued

Inhibition of neutral endopeptidases 24.11 and neutral proteinases 24.4 activities by phosphoramidon.

| Enzyme | Phosphoramidon (μM) | % Inhibition |
|---|---|---|
| B. cereus culture | 18.0 | ~95 |

Inhibition was measured at pH 7.5, 25° C., in the presence of 10 mM $CaCl_2$ except for the neutrophils that were assayed at 37° C. and in the absence of added $Ca^{2+}$. The substrate Suc-Ala-Ala-Leu-NH-Np at 0.4 mM was used. Endopeptidase 24.11 and thermolysin were used at $2.2 \times 10^{-9}$M and $1.5 \times 10^{-9}$M, respectively, human neutrophils at $5 \times 10^5$ cells/ml and B. cereus culture filtrate, 5 μl/ml substrate.

FIGURE LEGENDS

FIG. 5—Determination of the enzymatic activity of endopeptidase 24.11, using 0.4 mM Suc-Ala-Ala-Leu-NH-Np at pH 7.5. (o) The increase in absorbance at 405 nm upon addition of enzyme; Inhibition of the reaction by 1.8 μM phosphoramidon; Substrate, including the aminopeptidase, alone. Measurements were carried out in microplates continuously during 60 min periods. Each point represents an average of 4-6 wells.

We claim:

1. A substantially pure aminopeptidase obtained from *Streptomyces griseus* having the N-terminal sequence Ala-Pro-Asp-Ile-Pro-Leu, having an apparent molecular weight of (a) 33 kDa obtained from SDS-polyacrylamide gel electrophoresis and 21 kDa obtained from gel filtration on Superose 12 or (b) 34 kDa obtained from SDS-polyacrylamide gel electrophoresis and 22.5 kDa obtained from gel filtration on Superose 12, and containing 1.05 ±0.14 g atom of zinc per mole of said aminopeptidase.

2. The aminopeptidase of claim 1, wherein said aminopeptidase retains about 60% of it original enzymatic activity after heating five hours at 69° C. at pH 7.7.

3. The aminopeptidase of claim 2, wherein said aminopeptidase retains about 80% of its original enzymatic activity after heating five hours at 69° C. at pH 7.7 in the presence of $10^{-2}$M $CaCl_2$.

4. The aminopeptidase of claim 1, having an apparent molecular weight of 33 kDa obtained form SDS-polyacrylamide gel electrophoresis, and an apparent molecular weight of 21 kDa obtained from gel filtration on Superose 12.

5. The aminopeptidase of claim 1, having an apparent molecular weight of 34 kDa obtained from SDS-gel filtration, and an apparent molecular weight of 22.5 kDa obtained from gel filtration on Superose 12.

6. A process for purifying the aminopeptidase of claim 1, comprising the steps of:
   (i) dissolving protease type XIV in a buffer solution having a pH at which said aminopeptidase is stable and containing excess $Ca^{2+}$;
   (ii) heating said buffer solution at about 70° C. for a period of time sufficient to deactivate endopeptidase in said protease type XIV, thereby forming a precipitate;
   (iii) removing said precipitate from said solution;
   (iv) purifying said solution by (a) gel filtration or ultra filtration, followed by (b) ion exchange chromatography.

7. The process of claim 6, wherein the pH of said buffer solution is about 8.0.

8. The process of claim 6, wherein said heating step is conducted for about five hours.

9. The process of claim 6, wherein said removing step is conducted by centrifuging.

10. The process of claim 6, wherein said gel filtration is conducted using a Bio-Gel P-4 column.

11. The process of claim 6, wherein said purifying step is ion exchange chromatography conducted using DEAE-Sepharose.

12. The process of claim 6, wherein said purified solution is dialyzed against distilled water or buffer at a pH of about 5.5 prior to said isolating step.

* * * * *